United States Patent
Balaban et al.

(10) Patent No.: US 10,655,154 B2
(45) Date of Patent: May 19, 2020

(54) USE OF A CELLULOSE HYDROLYSATE FOR BIOGAS PRODUCTION

(71) Applicant: EPISOME BIYOTEKNOLOJIK ÜRÜNLER SANAYI VE TICARET ANONIM SIRKETI, Kocaeli (TR)

(72) Inventors: Murat Balaban, Kocaeli (TR); Murat Bahadir Kilinc, Kocaeli (TR)

(73) Assignee: EPISOME BIYOTEKNOLOJIK ÜRÜNLER SANAYI VE TICARET ANONIM SIRKETI, Kocaeli (TR)

( * ) Notice: Subject to any disclaimer, the term of this patent is extended or adjusted under 35 U.S.C. 154(b) by 170 days.

(21) Appl. No.: 15/576,286

(22) PCT Filed: May 26, 2016

(86) PCT No.: PCT/TR2016/050156
§ 371 (c)(1),
(2) Date: Nov. 22, 2017

(87) PCT Pub. No.: WO2016/209183
PCT Pub. Date: Dec. 29, 2016

(65) Prior Publication Data
US 2018/0155750 A1 Jun. 7, 2018

(30) Foreign Application Priority Data
Jun. 24, 2015 (TR) .................. 2015/07790

(51) Int. Cl.
*C12P 19/14* (2006.01)
*C12N 1/12* (2006.01)
*C12N 1/20* (2006.01)
*C12P 19/04* (2006.01)
*C12P 5/02* (2006.01)
*C12P 19/02* (2006.01)
*C13K 1/02* (2006.01)

(52) U.S. Cl.
CPC .............. *C12P 19/14* (2013.01); *C12N 1/20* (2013.01); *C12P 5/023* (2013.01); *C12P 19/02* (2013.01); *C12P 19/04* (2013.01); *C13K 1/02* (2013.01); *Y02E 50/343* (2013.01)

(58) Field of Classification Search
None
See application file for complete search history.

(56) References Cited

FOREIGN PATENT DOCUMENTS

| JP | S5398305 A | 8/1978 |
|---|---|---|
| WO | 2010037018 A2 | 4/2010 |
| WO | 2011092136 A1 | 8/2011 |

*Primary Examiner* — Yong D Pak
(74) *Attorney, Agent, or Firm* — Bayramoglu Law Offices LLC

(57) ABSTRACT

The present invention proposes a cellulose hydrolysis method including contacting a fermentation medium comprising paper sludge as carbon source with cellulase obtained on site from cellulase bacteria, until the mean glucose monomer number of cellulose molecules in the fermentation medium is decreased to a range between 5 and 500. The present invention further proposes a high-yield and low-cost method of biogas recovery from paper sludge.

5 Claims, No Drawings

USE OF A CELLULOSE HYDROLYSATE FOR BIOGAS PRODUCTION

CROSS REFERENCE TO RELATED APPLICATIONS

This application is the national phase entry of International Application PCT/TR2016/050156, filed on May 26, 2016, which is based upon and claims priority to Turkish Patent Application No. 2015/07790, filed on Jun. 24, 2015, the entire contents of which are incorporated herein by reference.

TECHNICAL FIELD OF THE INVENTION

The present invention relates to a method for cellulose hydrolysis and biogas production from hydrolyzed cellulose.

BACKGROUND OF THE INVENTION

It is important to optimize the economy of biogas production processes which recover cellulose-containing inlet materials such as paper sludge, or at least partly hydrolyzed cellulose-containing process intermediate streams. Such processes are usually dealing with bulk volumes due to high water contents in the streams. Accordingly, limited capacities at waste treatment in large scale facilities correspond to high setup costs due to volumetrically high water content in the cellulose-containing sludge.

JP S53 98 305 A is a prior art document related to the technical field of the present application.

Cellulose is a substrate that is hard to digest by microorganisms normally found in the flora of biogas reactors. The low digestibility of cellulose as is makes it a poor energy and carbon source, resulting in low yields in terms of biogas production.

Bacterial content of the processed material mixtures (e.g. during aeration in a lidless vessel) are difficult to control against spreading diseases and odor, by allowing growth of unwanted microorganisms causing disease and odor. Thus microbial invasion is a realistic concern as long as aerobic waste disposal methods are to be utilized for paper sludge disposal. Therefore suitable methods should be sought to process such microbial fluids with decreased water content.

Also high water content in such aqueous cellulose-containing mixtures requires big reactor volumes and also low reaction rates due to low concentration of reacting substances. There is a further drawback requiring improvement, that unprocessed cellulose-containing waste streams allow only low rates of biogas release, mainly due to mass transfer limitations related to low flowability. Obtainment of high yields with low process costs is difficult with current biogas production processes which use paper sludge related inlet streams.

Another drawback of using cellulose based materials as biogas raw material is low digestibility of cellulose by biogas producing bacterial consortia. Bacteria that are specialized for methane production are poor digesters of cellulose as is.

Heating and cooling of high water content streams require large amounts of energy. Furthermore, to obtain suitable fluidity, the streams are even diluted with large amounts of fresh water, which correspond to environmentally unfriendly methods, which is also a very important concern. High water content of streams to be aerated also increases aeration costs thereof.

Synthetic oil generation techniques like CatLiq, thermal gasification and pyrolysis require fluid materials pumped into very high pressure vessels. Paper sludge as it is in semi-dry form (from 10% dry matter content and above) forms aggregates and does not behave like a pumpable fluid.

Paper sludge cannot be used as soil amendments or fertilizer directly, due to unbalanced Nitrogen, Phosphorus and Potassium levels and long cellulose chains makes mixing of paper sludge with soil harder.

SUMMARY OF THE INVENTION

Primary object of the present invention is to overcome the abovementioned shortcomings of the prior art.

Another object of the present invention is provision of a method to obtain an intermediate product from paper sludge to be recovered in biogas production process.

A further object of the present invention is provision of a method to obtain a high yield and low cost process of biogas production from paper sludge.

Another objective of the present invention is provision of a method to obtain an intermediate product from paper sludge to be used in synthetic oil production via pyrolysis, thermal gasification or Catliq™ processes.

A further object of the present invention is provision of a method to obtain a product to be used in making compost from paper sludge in an accelerated manner.

The present invention proposes a cellulose hydrolysis method including contacting a fermentation medium comprising paper sludge as carbon source with cellulase obtained on site from cellulase bacteria, until the mean glucose monomer number of cellulose molecules in the fermentation medium is decreased to a range between 5 and 500. The present invention further proposes a high-yield and low-cost method of biogas recovery from paper sludge.

DETAILED DESCRIPTION OF THE INVENTION

The present invention proposes a cellulose hydrolysis method including the below step (Y):

Y) contacting a fermentation medium comprising paper sludge as carbon source with cellulase obtained on site from cellulase bacteria, until the mean glucose monomer number of cellulose molecules in the fermentation medium is decreased to a range between 5 and 500.

Preferably, the method includes the below step (X) prior to the step (Y):

X) bacteria production comprising the sequential steps (a-d) of:
  a) cultivation of bacteria (cellulolytic bacteria, preferably *cellulomonas*, more preferably *cellulomonas fimi*) from deep frozen stock into nutrient agar plates or Luria Broth plates, and incubating them at a temperature within the range between 30° C. and 40° C. for a first duration within the range between 1 day and 3 days,
  b) inoculation of a fermentation starter culture in liquid form with three or more colonies taken from said plates,
  c) incubation of the fermentation starter culture at a temperature within the range between about 30° C. and about 40° C. for a duration within the range between about 1 day and about 4 days,
  d) incubation of a production culture for a period within the range between 36 hours and 72 hours, started by mixing fermentation starter culture in an amount within the range between 1 wt. % and 10 wt. % with respect to the total weight of the production culture.

In a preferred alternative, at the step (d), the production culture comprises the below ingredients before the mixing with the fermentation starter culture:
- of beet molasses or cane molasses in an amount of 0.5 wt. % to 4 wt. %, with respect to the total volume of the production culture,
- NPK fertilizer (7-7-7) in an amount of 0.5 wt. % to 1.5 wt. %, with respect to the total weight of the production culture,
- of corn steep liquor in an amount of 0.15 wt. % to 0.5 wt. %, or yeast extract in an amount of 0.05 wt. % to 0.25 wt. %, or beer yeast waste in an amount of 0.05 wt. % to 0.25 wt. %, with respect to the total weight of the production culture, and at the culture, pH is kept at a value around 7.0, temperature is kept within a range between 30° C. and 40° C.

Possibly, biomass is harvested upon the end of the step (d) as a fluid product, by application of centrifuge corresponding to an acceleration on the production culture within a range between 29000 m/s$^2$ and 80000 g m/s$^2$, which values correspond to about 3000×g and 8000×g where g symbolizes gravitational acceleration (wherein g≈9.81 m/s$^2$).

Furthermore, this is possibly followed by drying of the biomass under air circulation at a temperature within the range between 40° C. and 50° C. until solid matter ratio in the biomass reaches to at least 90 wt % to obtain a solid product.

Preferably, the starter culture comprises Luria Broth, Nutrient Broth; or more preferably an aqueous nutritional medium (named as 'EpiMilk' by the inventors) prepared by mixing 0.5 wt. % to 2 wt. % of powdered milk, 0.5 wt. % to 2 wt. % of whey powder, 0.5 wt. % to 1 wt. % of sodium chloride, and 0.05 wt. % to 0.25 wt. % of corn steep liquor, with respect to the total weight of the nutritional medium, with an aqueous fluid. Accordingly, the present invention further proposes the above mentioned aqueous nutritional medium for growth of bacteria. This medium is a low cost mixture providing high efficiency at bacteria culture growth. Furthermore, the present invention further proposes the use of said nutritional medium as fermentation starter culture medium.

An exemplary application was performed according to the above method, and presented as 'Example A1'.

In a version of the method (which was presented as an exemplary application named 'Example A2'), the step (Y) comprises a hydrolysis step taking place in an aqueous mixture prepared by mixing paper sludge with a solid content within the range between 25 wt. % and 40 wt. %, with the following further ingredients added onto the paper sludge, amounts of the further ingredients being given per ton of the paper sludge:
- 5 kg to 10 kg of corn steep liquor, or 12.5 kg to 25 kg of beet molasses, or 2.5 kg to 5 kg of yeast extract, or 5 kg to 10 kg of beer yeast waste, or a mixture thereof;
- 50 g to 250 g of MgSO$_4$;
- 100 g to 200 g of the solid product, or 25 liters to 50 liters of the fluid product; further wherein said aqueous mixture is aerated at a temperature between 30° C. and 40° C. for a period between 24 hours and 72 hours, whilst maintaining the water content of the aqueous mixture, to obtain an output (A).

Part of the output (A) of this version of the method can be reserved to be used in hydrolysis of further batches, whereby the microorganisms in such part is grown in such further batches without additional microorganisms supply. To this end, the step (Y) comprises a hydrolysis step taking place in an aqueous mixture prepared by mixing paper sludge with a solid content within the range between 25 wt. % and 40 wt. %, with the following further ingredients added onto the paper sludge, amounts of the further ingredients being given per ton of the paper sludge:
- 300 kg to 350 kg of the output (A), containing cellulolytic microorganisms (cellulolytic bacteria, preferably cellulomonas);
- 6.5 kg to 13 kg of corn steep liquor, or 16.5 kg to 33 kg of beet molasses, or 3.75 kg to 6.5 kg of yeast extract, or 6.5 kg to 13 kg of beer yeast waste, or a mixture thereof;
- 65 g to 350 g of MgSO$_4$;
- 6.5 g to 13 g of the solid product, or 1.65 liters to 3.3 liters of the fluid product;
- further wherein said aqueous mixture is aerated at a temperature between 30° C. and 40° C. for a period between 24 hours and 72 hours, whilst maintaining the water content of the aqueous mixture, to obtain a hydrolyzed product (B) for use in biogas production.

In an alternative version of the method (which was presented as an exemplary application named 'Example A3'), the step (Y) comprises a hydrolysis step taking place in an aqueous mixture prepared by mixing paper sludge with a solid content within the range between 30 wt. % and 50 wt. %, with the following further ingredients added onto the paper sludge, amounts of the further ingredients being given per ton of the paper sludge:
- 20 kg to 40 kg of corn steep liquor, or 40 kg to 80 kg of beet molasses, or 10 kg to 20 kg of yeast extract, or 20 kg to 40 kg of beer yeast waste, or a mixture thereof;
- 100 g to 500 g of MgSO$_4$;
- 200 g to 400 g of the solid product, or 50 liters to 100 liters of the fluid product;
- water in an amount to drop the solid content of the aqueous mixture to a range between 8 wt. % and 15 wt. %;
- further wherein said aqueous mixture is aerated at a temperature between 30° C. and 40° C. for a period between 24 hours and 72 hours, whilst maintaining the water content of the aqueous mixture, to obtain a product (C). Then the aqueous mixture is subjected to a solid-liquid separation for obtainment of a fraction of hydrolyzed cellulose containing mixture with low liquid content and of a fluid fraction containing cellulolytic enzymes and cellulolytic microorganisms. In other words, the aqueous mixture is subjected to solid-liquid separation via filter press or decanter, leaving the cellulolytic enzymes and microorganisms in liquid fraction, making a liquid product. Separated solids are comprised of hydrolyzed cellulose containing paper sludge, which can be used in biogas production (and other processes like composting, synthetic oil etc).

Part of the product (C) of this version of the method can be reserved by separation using a separator (e.g. a filter press or a decanter) to separate a cellulolytic microorganism (bacteria) containing liquid fraction (Product C1) to be used in hydrolysis of further batches, to be used in hydrolysis of further batches, whereby the microorganisms in such part is grown in such further batches without additional microorganisms supply. The obtained solid part (e.g. in a filter press as mentioned above) contains hydrolyzed paper sludge, which can be used in biogas production (as a product C2). In such case, the step (Y) comprises a hydrolysis step taking place in an aqueous mixture prepared by mixing paper sludge with a solid content within the range between 30 wt.

% and 50 wt. %, with the following further ingredients added onto the paper sludge, amounts of the further ingredients being given per ton of the paper sludge:
- 2000 kg to 3000 kg of the product (C1), containing cellulolytic microorganisms;
- 400 kg to 600 kg of water;
- 20 kg to 40 kg of corn steep liquor, or 40 kg to 80 kg of beet molasses, or 10 kg to 20 kg of yeast extract, or 20 kg to 40 kg of beer yeast waste, or a mixture thereof;
- 100 g to 500 g of $MgSO_4$;
- 16 g to 32 g of the solid product, or 4 liters to 8 liters of the fluid product;

further wherein said aqueous mixture is aerated at a temperature between 30° C. and 40° C. for a period between 24 hours and 72 hours, whilst maintaining the water content of the aqueous mixture, to obtain a hydrolyzed product (D) for use in biogas production.

Accordingly, the present invention further proposes the use of the hydrolyzed products (B or D) in biogas production (which was presented as an exemplary application named 'Example B1'). To this end, a further step (Z) is proposed, which comprises mixing the hydrolyzed product (B and/or D) with a solid content within the range between 30 wt. % and 40 wt. % (i.e. the solid content of the product B and/or D is arranged to such values by water addition or removal), with the following further ingredients added onto the hydrolyzed product, amounts of the further ingredients being given per kilogram of the hydrolyzed product:
- 0.5 kg to 1.5 kg of poultry manure with 20 wt. % to 30 wt. % of solid content,
- 20 kg to 30 kg of a biogas reactor sludge with 7 wt. % to 8 wt. % of solid content further wherein this mixture is incubated under anaerobic conditions at a temperature between 35° C. and 40° C. for a period between 7 days and 12 days, and preferably mixed intermittently.

EXAMPLES

The invention has been described with reference to various example embodiments. Example A1

As step (X), bacteria production was performed prior to the step (Y) by following sequential steps (corresponding to steps (a) to (d):
a) bacteria from deep frozen stock at −80° C. was cultivated into nutrient agar plates, and incubated at 35° C. for a first duration of 2 days,
b) a fermentation starter culture in liquid form was inoculated with three colonies taken from said plates,
c) the fermentation starter culture was incubated at 35° C. for a duration of 3 days,
d) a production culture was incubated for a period 48 hours, started by mixing fermentation starter culture in an amount of 5 wt. % with respect to the total weight of the production culture.

At the step (d), the production culture comprised the below ingredients before the mixing with the fermentation starter culture:
- of beet molasses in an amount of 2.5% (v/v), with respect to the total volume of the production culture,
- of NPK fertilizer (7-7-7) in an amount of 1 wt. %, with respect to the total weight of the production culture,
- of corn steep liquor in an amount of 0.35 wt. % with respect to the total weight of the production culture, and at the culture, pH is kept at a value around 7.0, temperature is kept at about 35° C. Biomass is harvested upon the end of the step (d) as a fluid product, by application of centrifuge corresponding to an acceleration on the production culture of about 5000 g (corresponding to about 49050 m/s², where the acceleration of gravity g corresponds to 9.81 m/s²). This is followed by drying of the biomass under air circulation at about 47° C. until solid matter ratio in the biomass reaches to 90 wt % to obtain a solid product.

As starter culture, the aqueous nutritional medium was used (named as 'EpiMilk' by the inventors) which is prepared by mixing 1 wt. % of powdered milk, 1 wt. % of whey powder, 0.5 wt. % of sodium chloride, and 0.15 wt. % of corn steep liquor, with respect to the total weight of the nutritional medium, with an aqueous fluid.

Example A2

In this example, the step (Y) comprised a hydrolysis step taking place in an aqueous mixture prepared by mixing 20 kg of paper sludge with a solid content of 30 wt. %, with the following further ingredients added onto the paper sludge:
- 150 g of corn steep liquor;
- 3 g of $MgSO_4$;
- 3 g of the solid product;

and said aqueous mixture was aerated at a temperature of 35° C. for a period of 48 hours, whilst maintaining the water content of the aqueous mixture, to obtain a output (A) (i.e. a hydrolysed cellulosic substance) containing cellulolytic microorganisms.

Part of the output (A) was reserved to be used in hydrolysis of a further batch, whereby the microorganisms in that part was grown in the further batch without requiring additional microorganism to be supplied. To this end, the step (Y) comprised a hydrolysis step taking place in an aqueous mixture prepared by mixing 15 kg of paper sludge with a solid content of 35 wt. %, with the following further ingredients added onto the paper sludge:
- 5 kg of the output (A), containing cellulolytic microorganisms;
- 150 g of corn steep liquor;
- 3 g of $MgSO_4$;
- 150 g of the solid product;

further wherein said aqueous mixture is aerated at a temperature of 35° C. for a period of 48 hours, whilst maintaining the water content of the aqueous mixture, to obtain a hydrolyzed product (B) for use in biogas production.

Example A3

As an example to test the latter method, the step (Y) comprised a hydrolysis step taking place in an aqueous mixture prepared by mixing 10 kg of paper sludge with a solid content of 40 wt. %, with the following further ingredients added onto the paper sludge, amounts of the further ingredients being given per ton of the paper sludge:
- 300 g of corn steep liquor;
- 3 g of $MgSO_4$;
- 1 liter of the fluid product (corresponding to about 4 grams of dried or solid product);
- 30 kg of water to drop the solid content of the aqueous mixture to about 10 wt. %;

further wherein said aqueous mixture is aerated at a temperature of 35° C. for a period of 48 hours, whilst maintaining the water content of the aqueous mixture, to obtain a product (C) (i.e. hydrolysed cellulose) containing cellulolytic microorganisms.

Part of the product (C) of this version of the method was reserved to be used in hydrolysis of a further batch, whereby the microorganisms in that part was grown in the further batch without requiring additional microorganisms to be supplied. To this end, the step (Y) comprised a hydrolysis step taking place in an aqueous mixture prepared by mixing 10 kg of paper sludge with a solid content of 40 wt. %, with the following further ingredients added onto the paper sludge:

- 25 kg of the product (C), containing cellulolytic microorganisms;
- 5 kg of well water (considered suitable to be replaced with city water or demineralized water in all cases in the methods according to the present invention);
- 200 g of corn steep liquor (considered suitable to be replaced with 400 g or more of beet molasses, or 100 g or more of yeast extract, or 100 g or more of beer yeast waste, or a mixture thereof in all cases in the methods according to the present invention);
- 3 g of $MgSO_4$;
- 160 mg of the solid product, (considered suitable to be replaced with about 4 liters or more of the fluid product in all cases in the methods according to the present invention);

and then this aqueous mixture was aerated at a temperature of 35° C. for a period of 48 hours, whilst maintaining the water content of the aqueous mixture, to obtain a hydrolyzed product (D) for use in biogas production.

Example B1

For the sake of carbon and nitrogen balance, 3.75 kg of carbon-rich paper sludge with 35 wt. % solid matter with respect to the total weight of the paper sludge, was mixed with 3.75 kg of nitrogen-rich chicken manure with 25 wt. % solid content with respect to the total weight of the chicken manure. This mixture was added to 92.5 kg of a biogas reactor sludge with 7.5 wt. % of solid content with respect to the total weight of the biogas reactor sludge, thus a mixture with a total weight of 100 g is obtained; and then incubated under anaerobic conditions at a temperature of 39° C. for a period of 10 days, and mixed intermittently for periods of 1 minute every 1 hour. 880 liters of biogas output was obtained throughout the experiment, from 3.75*35/100=1.3125 kg of cellulose-based solid content, which corresponds to about 670 liters of biogas production per kg of cellulose-based solid content. This shows a great improvement with regard to the comparative examples, especially to the Comparative Example C2 where artificial urea is used instead of product B and/or D.

Comparative Example C1

A comparative example was designed to evaluate the ability of paper sludge to convert into biogas without addition of hydrolyzed product (B and/or D). To this end, 5 kg of carbon-rich paper sludge with 35 wt. % of solid content with respect to the total weight of the paper sludge was added to 95 kg of a biogas reactor sludge with 7.5 wt. % of solid content with respect to the total weight of the biogas reactor sludge, thus a mixture with a total weight of 100 g is obtained; and then incubated under anaerobic conditions at a temperature of 39° C. for a period of 20 days, and mixed intermittently for 1 minute every 1 hour. 550 liters of biogas was obtained throughout the experiment, from 5*35/100=1.75 kg of cellulose-based solid content, which corresponds to only about 314 liters of biogas production per kg of cellulose-based solid content. Thus a significantly lower and slower conversion to biogas occurs at the Comparative Example C1 when compared with the Example B1.

Comparative Example C2

A further comparative example was designed to evaluate the ability of paper sludge to convert into biogas by addition of artificial carbon and nitrogen source (urea), instead of addition of hydrolyzed product (B and/or D). To this end, 5 kg of carbon-rich paper sludge with 35 wt. % of solid content with respect to the total weight of the paper sludge was mixed with 37.5 g of urea, and then added to 95 kg of a biogas reactor sludge with 7.5 wt. % of solid content with respect to the total weight of the biogas reactor sludge, thus a mixture with a total weight of about 100 g is obtained; and then incubated under anaerobic conditions at a temperature of 39° C. for a period of 10 days, and mixed intermittently for 1 minute every 1 hour. 650 liters of biogas was obtained throughout the experiment, from 5*35/100=1.75 kg of cellulose-based solid content, which corresponds to about 371 liters of biogas production per kg of cellulose-based solid content. Thus a still significantly lower conversion to biogas occurs at the Comparative Example C2 when compared with the Example B1.

The present invention enables achieving low viscosity (related to improved pumpability) in suspensions containing in high concentrations of cellulose, which is important to decrease unnecessary water usage, to decrease energy consumptions in processes, and enables pumpability (i.e. easy transportation of material via pumps) in industrial environments and further enables better packing of substrate when pressed e.g. using a filter or belt press. The present invention is further advantageous by decreasing volumetric requirements and finally increasing the biogas yield per unit of organic matter.

That the mean glucose monomer number of cellulose molecules in the fermentation medium is decreased to a range between 5 and 500 can be followed by measuring the viscosity of the medium. At the experiments, it is observed that the dynamic viscosity of the medium (having a dry matter content of 10 wt. %) decreased from about 30000 cP (centiPoise, where a Poise corresponds to 1 $kg·m^{-1}·s^{-1}$) to about a range between 3000 and 4000 cP throughout the hydrolysis process. It is even possible to reduce the dynamic viscosity of the medium throughout the process according to the present invention, to about one hundredth of that at the beginning of the process. Yet, some other factors such as presence of clay etc in the medium can result in deviations of validity of the measured viscosity values. The mean number of glucose subunits (mean glucose monomer number) can also be more realistically measured by various analytical methods such as mass spectroscopy.

As achieved with the method according to the present invention, decreasing the viscosity of cellulose containing fluid material and thus rendering it pumpable can make synthetic oil generation techniques like CatLiq, thermal gasification, and pyrolysis more feasible. Processing paper sludge (as an example to cellulose containing fluid materials) through an anaerobic digestion chamber as in the method of present invention, paper sludge is converted nutritionally balanced compost, which supports microbial growth in the soil.

Thus the following objects are achieved by the present invention:

- overcoming the abovementioned shortcomings of the prior art, provision of:
- a method to obtain an intermediate product from paper sludge to be recovered in biogas production process.
- a method to obtain a high yield and low cost process of biogas production from paper sludge
- an environmentally friendly method with decreased water consumption in cellulose hydrolysis and biogas recovery therefrom
- facilitated aeration of cellulose-containing sludge thanks to its decreased water content,
- reduced risk of microbial invasion thanks to increased viscosity cellulose-containing sludge as a result of decreased water content,
- decreased setup costs and high capacity at waste treatment in smaller scale facilities thanks to volumetrically decreased water content in the cellulose-containing sludge,
- increased yield in biogas production from cellulosic material, thanks to predigested cellulose chains ending-up in shorter cellulose chains and higher utilization by biogas producing microbial flora.

What is claimed is:

1. A cellulose hydrolysis method comprising: a step (Y) including contacting a fermentation medium having paper sludge which is used as a carbon source with cellulase secreted from *cellulomonas fimi* bacteria while living on the fermentation medium until the mean glucose monomer number of cellulose molecules in the fermentation medium is decreased to a range between 5 and 500;
   a step (X) for production of *cellulomonas fimi* bacteria implemented prior to the step (Y), the step (X) including the sequential steps in the order of:
   a) cultivating the *cellulomonas fimi* bacteria from deep frozen stock into one or more nutrient agar plates or one or more luria broth plates, and incubating the *cellulomonas fimi* bacteria at a temperature within a range between 30° C. and 40° C. for a duration between 1 day and 3 days,
   b) inoculating a fermentation starter culture in liquid form with three or more colonies taken from the nutrient agar plates or the luria broth plates,
   c) incubating the fermentation starter culture inoculated with three or more colonies of step b) at a temperature within the range between about 30° C. and about 40° C. for a duration between about 1 days and about 4 days,
   d) incubating a production culture for a period within a range between 36 hours and 72 hours, wherein the incubation is started by preparing a production culture which includes the fermentation starter culture inoculated with three or more of step b) colonies in an amount within a range between 1 wt. % and 10 wt. % with respect to the total weight of the production culture;
   e) harvesting biomass upon the end of the step (d) as a fluid product, applying a centrifuge corresponding to an acceleration on the production culture of step d), wherein the production culture includes the fermentation starter culture inoculated with three or more colonies of step b) in an amount within a range between 1 wt. % and 10 wt. % with respect to the total weight of the production culture of step d), within a range between 29000 m/s$^2$ and 80000 g m/s$^2$;

wherein, the step (Y) is a hydrolysis step in which the hydrolysis is carried out after contacting a fermentation medium, the hydrolysis step taking place in an aqueous mixture prepared by mixing the paper sludge with a solid matter within the range of biomass between 25 wt. % and 40 wt. %, with the following further ingredients added onto the paper sludge, amounts of the further ingredients being given per ton of the paper sludge is in the order as below:
   5 kg to 10 kg of corn steep liquor, or 12.5 kg to 25 kg of beet molasses, or 2.5 kg to 5 kg of yeast extract, or 5 kg to 10 kg of beer yeast waste, or a mixture thereof;
   50 g to 250 g of $MgSO_4$;
   100 g to 200 g of the solid product of the biomass wherein the biomass is dried, or 25 liters to 50 liters of the fluid product comprising the harvested biomass;
   wherein the aqueous mixture is aerated at a temperature between 30° C. and 40° C. for a period between 24 hours and 72 hours, whilst maintaining a water content of the aqueous mixture.

2. The cellulose hydrolysis method according to the claim 1,
   wherein in step (d) the production culture comprises the below ingredients before being mixed with the fermentation starter culture:
      beet molasses or cane molasses in an amount of 0.5 wt. % to 4 wt. %, with respect to the total volume of the production culture,
      NPK fertilizer (7-7-7) in an amount of 0.5 wt. % to 1.5 wt. %, with respect to the total weight of the production culture,
      corn steep liquor in an amount of 0.15 wt. % to 0.5 wt. %, or yeast extract in an amount of 0.05 wt. % to 0.25 wt. %, or beer yeast waste in an amount of 0.05 wt. % to 0.25 wt. %, with respect to the total weight of the production culture,
   and at the production culture, wherein during the production culture pH is kept at a value around 7.0 and temperature is kept within a range between 30° C. and 40° C.

3. The cellulose hydrolysis method according claim 1, wherein the fermentation starter culture comprises the luria broth, the nutrient broth or an aqueous nutritional medium made by mixing 0.5 wt. % to 2 wt. % of powdered milk, 0.5 wt. % to 2 wt. % of whey powder, 0.5 wt. % to 1 wt. % of sodium chloride, and 0.05 wt. % to 0.25 wt. % of corn steep liquor, with respect to the total weight of the nutritional medium, with an aqueous fluid.

4. The cellulose hydrolysis method according to claim 2, wherein the fermentation starter culture comprises the luria broth, the nutrient broth or preferably an aqueous nutritional medium made by mixing 0.5 wt. % to 2 wt. % of powdered milk, 0.5 wt. % to 2 wt. % of whey powder, 0.5 wt. % to 1 wt. % of sodium chloride, and 0.05 wt. % to 0.25 wt. % of corn steep liquor, with respect to the total weight of the nutritional medium, with an aqueous fluid.

5. The cellulose hydrolysis method according claim 1, further comprising, drying the biomass under an air circulation at a temperature within a range between 40° C. and 50° C. until a solid matter ratio in the biomass reaches to at least 90 wt % to obtain a solid product.

* * * * *